United States Patent
Amann et al.

(10) Patent No.: US 10,835,121 B2
(45) Date of Patent: *Nov. 17, 2020

(54) TRANSMITTING TREATMENT INFORMATION

(71) Applicant: ZOLL Medical Corporation, Chelmsford, MA (US)

(72) Inventors: John Amann, Worcester, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 83 days.

This patent is subject to a terminal disclaimer.

(21) Appl. No.: 16/190,661

(22) Filed: Nov. 14, 2018

(65) Prior Publication Data

US 2019/0143134 A1    May 16, 2019

Related U.S. Application Data

(63) Continuation of application No. 15/706,994, filed on Sep. 18, 2017, now Pat. No. 10,159,848, which is a (Continued)

(51) Int. Cl.
| | |
|---|---|
| *A61N 1/39* | (2006.01) |
| *A61B 5/00* | (2006.01) |
| *A61B 5/04* | (2006.01) |
| *A61B 5/0404* | (2006.01) |
| *A61N 1/02* | (2006.01) |
| *G06F 19/00* | (2018.01) |

(Continued)

(52) U.S. Cl.
CPC .......... *A61B 5/0006* (2013.01); *A61B 5/0404* (2013.01); *A61B 5/04012* (2013.01); *A61N 1/025* (2013.01); *A61N 1/3904* (2017.08); *A61N 1/3931* (2013.01); *A61N 1/3937* (2013.01); *A61N 1/39044* (2017.08); *A61N 1/3968* (2013.01); *A61N 1/3987* (2013.01); *A61N 1/3993* (2013.01); *G06F 19/00* (2013.01); *A61B 5/053* (2013.01); *A61B 5/4848* (2013.01); *G06Q 50/22* (2013.01)

(58) Field of Classification Search
USPC ................................................. 600/508, 509
See application file for complete search history.

(56) References Cited

U.S. PATENT DOCUMENTS

| | | |
|---|---|---|
| 9,795,800 B2 | 10/2017 | Amann et al. |
| 2006/0219776 A1 | 10/2006 | Finn |

(Continued)

OTHER PUBLICATIONS

International Search Report & Written Opinion, PCT/US2014/057833, dated Mar. 3, 2015, 14 pages.

(Continued)

*Primary Examiner* — Nicole F Lavert
(74) *Attorney, Agent, or Firm* — Fish & Richardson P.C.

(57) ABSTRACT

A system includes a first computing device comprising a processor coupled to a memory. The processor and the memory are configured to receive at least one of (i) information indicative of treatment of a victim by a first caregiver using the first computing device and (ii) information indicative of a health status of the victim; determine that treatment of the victim by the first caregiver using the first computing device is completed; and transmit the received information to a second computing device.

30 Claims, 13 Drawing Sheets

Related U.S. Application Data continuation of application No. 15/271,388, filed on Sep. 21, 2016, now Pat. No. 9,795,800, which is a continuation of application No. 14/498,595, filed on Sep. 26, 2014, now Pat. No. 9,474,446, which is a continuation-in-part of application No. 14/039,727, filed on Sep. 27, 2013, now Pat. No. 9,144,390.

(51) Int. Cl.
  *G06Q 50/22* (2018.01)
  *A61B 5/053* (2006.01)

(56) References Cited

U.S. PATENT DOCUMENTS

| | | | |
|---|---|---|---|
| 2010/0234910 A1* | 9/2010 | Parascandola | G09B 23/288 607/5 |
| 2010/0297594 A1* | 11/2010 | Sullivan | A61B 5/0002 434/262 |
| 2011/0060378 A1 | 3/2011 | Tuysserkani | |
| 2011/0172550 A1 | 7/2011 | Martin et al. | |
| 2011/0202100 A1* | 8/2011 | Tan | A61H 31/005 607/6 |
| 2012/0071942 A1* | 3/2012 | Kamath | A61N 1/3987 607/14 |
| 2012/0123224 A1 | 5/2012 | Packer et al. | |
| 2018/0154163 A1 | 6/2018 | Amann | |

OTHER PUBLICATIONS

Office Action in U.S. Appl. No. 15/706,994, dated Apr. 5, 2018, 7 pages.

\* cited by examiner

TRANSMITTING TREATMENT INFORMATION

CLAIM OF PRIORITY

This application is a continuation of and claims priority under 35 U.S.C. § 120 to U.S. patent application Ser. No. 15/706,994, filed on Sep. 18, 2017, which is a continuation of and claims priority to U.S. patent application Ser. No. 15/271,388, filed on Sep. 21, 2016, now U.S. Pat. No. 9,795,800, which is a continuation of and claims priority to U.S. patent application Ser. No. 14/498,595, filed on Sep. 26, 2014, now U.S. Pat. No. 9,474,446, which is a continuation-in-part of and claims priority to U.S. patent application Ser. No. 14/039,727, filed on Sep. 27, 2013, now U.S. Pat. No. 9,144,390. The entire contents of each application is hereby incorporated by reference.

TECHNICAL FIELD

This invention relates to transmission and storage of information indicative of the performance of a caregiver treating a victim and information indicative of a health status of the victim. In some examples, portions of an electrocardiogram (ECG) trace can be identified, for instance, portions of ECG traces of a victim treated by a defibrillating system such as an automated external defibrillator (AED).

BACKGROUND

Sudden health problems such as sudden cardiac arrest and injuries caused by accidents kill thousands of people and cause permanent injury every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy. Along with such action, an electrocardiogram (ECG) signal for the patient may be electronically captured, displayed, and monitored, so that rescuers can determine when the patient's heart has returned to normal or near-normal operation, and determine when the heart exhibits a shockable rhythm.

SUMMARY

In a general aspect, a system includes a first computing device comprising a processor coupled to a memory. The processor and the memory are configured to receive at least one of (i) information indicative of treatment of a victim by a first caregiver using the first computing device and (ii) information indicative of a health status of the victim; determine that treatment of the victim by the first caregiver using the first computing device is completed; and transmit the received information to a second computing device.

Embodiments can include one or more of the following features.

Receiving the information indicative of treatment of the victim includes detecting a characteristic of the treatment of the victim by the first caregiver. In some cases, the characteristic of the treatment includes one or more of a depth of chest compressions, a rate of chest compressions, a duration of chest compressions, and an indication of a continuity of chest compressions.

Receiving the information indicative of a health status of the victim includes detecting a characteristic of the health status of the victim. In some cases, the characteristic of the health status includes one or more of a vital sign of the victim and an ECG trace of the victim.

Determining that treatment of the victim by the first caregiver using the first computing device is completed includes detecting an indication that treatment is completed. In some cases, detecting an indication that treatment is completed includes detecting that the first computing device has been disconnected from the victim. In some cases, determining that treatment of the victim by the first caregiver using the first computing device is completed includes receiving an input from the first caregiver. In some cases, determining that treatment of the victim by the first caregiver using the first computing device is completed includes receiving a signal from the second computing device.

The first computing device includes a defibrillator or a mobile computing device. The second computing device includes a defibrillator or a server.

Transmitting the received information includes transmitting the received information to the second computing device according to a secure communications protocol. In some cases, a key is transmitted to the second computing device. In some cases, the key is based on an identifier of the victim and an identifier of the first device. In some cases a key enabling a third computing device to access the information transmitted to the second computing device is transmitted to the third computing device.

The first computing device is configured to transmit the received information after a primary functionality of the first computing device has been turned off.

In a general aspect, a method includes receiving at least one of (i) information indicative of treatment of a victim by a first caregiver using the first computing device and (ii) information indicative of a health status of the victim; determining that treatment of the victim by the first caregiver using the first computing device is completed; and transmitting the received information to a second computing device.

In a general aspect, a computer readable medium stores instructions for causing a computing system to receive at least one of (i) information indicative of treatment of a victim by a first caregiver using the first computing device and (ii) information indicative of a health status of the victim; determine that treatment of the victim by the first caregiver using the first computing device is completed; and transmit the received information to a second computing device.

In a general aspect, a defibrillating system includes a processor coupled to a memory. The processor and the memory are configured to identify a treatment event associated with treatment of a victim with the defibrillating system, and transmit a representation of a portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The processor and the memory are configured to identify the portion of the ECG signal associated with the identified treatment event. In some cases, identifying the portion of the ECG signal comprises selecting a portion of the ECG signal having a predetermined length of time.

The processor and the memory are configured to identify multiple treatment events associated with treatment of the victim with the defibrillating system. In some cases, the processor and the memory are configured to transmit an identifier of each of the multiple treatment events. In some cases, the processor and the memory are configured to receive a selection of a particular one of the multiple treatment events. In some cases, the processor and the memory are configured to transmit the portion of the ECG signal associated with the particular one of the multiple treatment events.

Transmitting the portion of the ECG signal includes displaying the portion of the ECG signal on a display interface of the defibrillating system.

Transmitting the portion of the ECG signal includes transmitting the portion of the ECG signal to a computing device.

The processor and the memory are configured to detect that the defibrillating system has been disconnected from the victim. In some cases, the processor and the memory are configured to detect that the defibrillating system has been disconnected by detecting a loss of impedance in a circuit that includes the defibrillating system and the victim.

The portion of the ECG signal corresponds to a time period in which the defibrillating system performed an analysis of the victim's rhythm.

The portion of the ECG signal corresponds to a time period during which the defibrillating system was first connected to the victim.

In a general aspect, a defibrillating system includes a processor coupled to a memory. The processor and the memory are configured to, during treatment of a victim with an automated external defibrillator (AED), associate each of multiple portions of an electrocardiogram (ECG) signal with a corresponding treatment event. The processor and the memory are configured to detect that the AED has been disconnected from the victim; responsive to the disconnection of the AED, display identifiers of at least some of the treatment events; receive a user selection of one of the displayed treatment events; and display a representation of the portion of the ECG signal associated with the selected treatment event.

In a general aspect, a method includes identifying, by a processor of a defibrillating system, a treatment event associated with treatment of a victim with the defibrillating system; and transmitting, by the processor, a representation of a portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The defibrillating system includes an AED

The method includes identifying the portion of the ECG signal associated with the identified treatment event. In some cases, identifying the portion of the ECG signal includes selecting a portion of the ECG signal having a predetermined length of time.

Identifying a treatment event includes identifying multiple treatment events associated with treatment of the victim with the defibrillating system. In some cases, the method includes transmitting an identifier of each of the multiple treatment events. In some cases, the method includes receiving a selection of a particular one of the multiple treatment events. In some cases, the method includes transmitting the portion of the ECG signal comprises transmitting the portion of the ECG signal associated with the particular one of the multiple treatment events.

Transmitting the portion of the ECG signal comprises displaying the portion of the ECG signal on a display interface of the defibrillating system.

Transmitting the portion of the ECG signal comprises transmitting the portion of the ECG signal to a computing device.

The method includes detecting that the defibrillating system has been disconnected from the victim. In some cases, detecting that the defibrillating system has been disconnected includes detecting a loss of impedance in a circuit that includes the defibrillating system and the victim. In some cases, the method includes receiving confirmation from the user that the defibrillating system has been disconnected.

In a general aspect, a computer readable medium stores instructions for causing a computing system to identify a treatment event associated with treatment of a victim with the defibrillating system, and transmit a representation of portion of an ECG signal associated with the identified treatment event.

Embodiments may include one or more of the following features.

The portion of the ECG signal is of a predetermined length of time having a start time and an end time based on a time associated with the identified treatment event. In some cases, the predetermined length of time is less than about 15 seconds.

The instructions cause the computing system to identify the portion of the ECG signal associated with the identified treatment event. In some cases, identifying the portion of the ECG signal includes selecting a portion of the ECG signal having a predetermined length of time.

The instructions cause the computing system to identify multiple treatment events associated with treatment of the victim with the defibrillating system. In some cases, the instructions cause the computing system to receive a selection of a particular one of the multiple treatment events. In some cases, the instructions cause the computing system to transmit the portion of the ECG signal associated with the particular one of the multiple treatment events.

The techniques described herein can have one or more of the following advantages. Storing information about treatment delivered to a victim by an early caregiver can help inform the treatment of the victim by a later caregiver, even if that caregiver was not present for the early treatment. For instance, monitoring and storing portions of a victim's ECG trace on a defibrillating system, such as an automated external defibrillator (AED), allows a caregiver to view information about the victim's cardiac rhythm at a later point in time, which can aid in diagnosing and treating the victim. For instance, re-displaying a portion of the victim's ECG trace from a point in time when treatment was started and/or a portion of the victim's ECG trace prior to receiving a shock can provide information that can be used to diagnose the victim's condition. Knowledge of the victim's likely diagnosis can inform treatment of the victim, both at the rescue scene and in a hospital setting. The ability to view the historical information about treatment and health status of the victim at the rescue scene or at another location, such as at a hospital, can enable skilled caregivers to make informed treatment decisions even if those caregivers were not present when the information was recorded.

The details of one or more embodiments are set forth in the accompanying drawings and the description below. Other features and advantages will be apparent from the description, drawings, and claims.

DETAILED DESCRIPTION

Figure 1A:
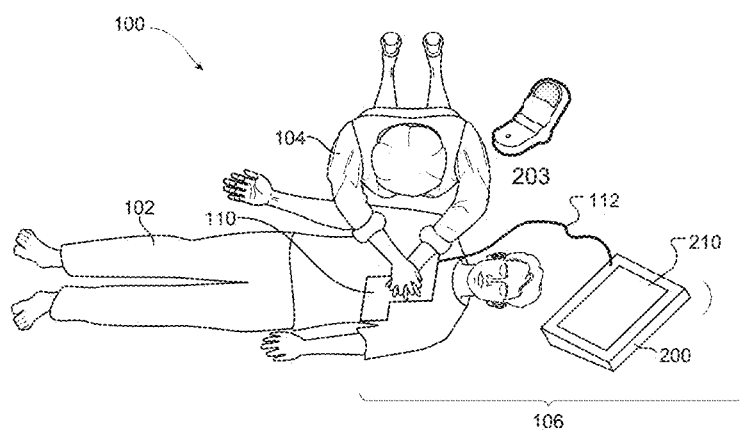
FIGS. 1A and 1B are diagrams of a rescue scene.

At a rescue scene, one or more caregivers may deliver treatment to a victim. We describe here an approach to collecting, storing, and transmitting information indicative of the performance of the caregivers, the health status of the victim, or both. For instance, the information indicative of the performance of the caregivers can include, e.g., information about the quality of chest compressions delivered to the victim, the duration of cardiopulmonary resuscitation (CPR), or other information. The information indicative of the health status of the victim can include, e.g., the victim's vital signs, one or more portions of the victim's electrocardiogram (ECG) trace, or other information.

The information can be transmitted to and displayed on a display interface of a defibrillator, transmitted to one or more local or remote computing devices for storage or display, or otherwise transmitted. In some examples, the information can be displayed on a defibrillator, such as an AED, at the rescue scene, e.g., so that a trained professional rescuer taking over care of the victim from a first responder can review the performance of the first responder. In some examples, the information can be transmitted to a computing device for viewing by a person away from the rescue scene, such as a coordinator at a dispatch center, a medical professional at an emergency room, or another person. In some examples, the information can be transmitted to a storage device, such as a database hosted by a cloud server, so that the information can later be accessed and viewed, e.g., by an emergency room professional, the victim's primary care doctor, or another person.

The ability to view information indicative of the performance of the caregivers and/or information indicative of the health status of the victim at the rescue scene can provide critical, lifesaving information to the victim's caregivers. As the victim is transferred to higher levels of care, information about the victim's health and treatment can be made accessible to and/or presented to the professionals providing that care. For instance, an initial caregiver may be a relatively untrained caregiver, such as a police officer or firefighter. As such, the initial caregiver may be unable to communicate detailed information about his performance (e.g., the duration or quality of the chest compressions he delivered to the victim) or the victim's health status to a more highly trained caregiver that may arrive on the scene later. By providing the trained caregiver with the ability to view historical information indicative of the performance of an earlier caregiver and/or information indicative of the health status of the victim, the trained caregiver can have rapid access to information that can enable him to make more informed decisions about treatment options for the victim (e.g., information about the victim's condition when he first collapsed or information about the rhythms that triggered shock events). For instance, the caregiver can use this information to decide which medications to administer, whether to initiate or continue with CPR or defibrillation treatment, how urgently to bring the victim to an emergency room, or other decisions. Similarly, other medical personnel, such as emergency room nurses or physicians, can also use the information indicative of the performance of the caregivers and/or the information indicative of the health status of the victim to make informed decisions about treating the victim.

In some examples, one or more portions of a victim's ECG trace are collected, stored, and transmitted. The portions of the victim's ECG trace can be transmitted at a time subsequent to collecting and storing the ECG trace, such as upon request by a user of a defibrillator, such as an AED, during treatment of the victim or upon disconnecting the AED from the victim. For instance, the portions of the victim's ECG trace can be transmitted to a display interface of the AED for display, transmitted to a local or remote computing device for storage or display, or otherwise transmitted. It can be beneficial for a rescuer or medical professional to have access to information about earlier portions of the victim's ECG to aid in diagnosis and/or treatment of the victim. For instance, the portions of the victim's ECG trace can be associated with treatment events, such as determinations by the AED of whether the victim's cardiac rhythm was shockable or non-shockable. In one example, the portion of the victim's ECG trace when treatment was started and/or the portions of the victim's ECG trace prior to receiving a shock (or prior to a determination that the victim's rhythm was non-shockable) can be displayed on the AED, providing information that can be used by a caregiver to diagnose the victim's condition and/or to inform treatment decisions.

The ability to view portions of the victim's ECG trace at the rescue scene can provide critical, lifesaving information to a victim's caregivers. For instance, an initial caregiver may be a relatively untrained caregiver, such as a police officer, who does not know how to read ECG traces. As such, the initial caregiver may be unable to communicate information about the victim's initial ECG trace and information about portions of the ECG trace in the analysis periods to a highly trained caregiver that may arrive on the scene later. By providing the trained caregiver with the ability to view portions of the victim's ECG trace, the trained caregiver can have rapid access to information that can enable him to make more informed decisions about treatment options for the victim (e.g., information about the victim's condition when he first collapsed or information about the rhythms that triggered shock events). For instance, the caregiver can use this information to decide which medications to administer, whether to continue with CPR or defibrillation treatment, how urgently to bring the victim to an emergency room, and other decisions. In addition, the caregiver can communicate this information to other medical personnel, such as emergency room nurses or physicians, without having to download the ECG traces or transport the AED itself to the emergency room.

Referring to FIG. 1A, at a rescue scene 100, a caregiver 104 performs cardiopulmonary resuscitation (CPR) on a victim 102. The victim 102 may be, for instance, an individual who has apparently undergone sudden cardiac arrest. The caregiver 104 may be, for instance, a civilian responder with limited or no training in lifesaving techniques; a first responder, such as a police officer, firefighter, emergency medical technician (EMT), or paramedic; or a medical professional, such as a physician or nurse. The caregiver 104 may be acting alone or may be acting with assistance from one or more other caregivers, such as a partner police officer. Although FIG. 1A is described with respect to a rescue scene 100, the approaches described here can also be used in other situations, such as in a medical treatment facility such as an emergency room, hospital, medical clinic, or other type of facility.

A computing device at the rescue scene 100 can store information indicative of the performance of the caregiver 104 when delivering treatment to the victim 102, the health status of the victim 102, or both. The computing device that stores the information can be an electronic defibrillating system 106 that includes a defibrillator 200, such as an automated external defibrillator (AED), a professional defibrillator, or another type of defibrillating apparatus. The computing device that stores the information can be a mobile computing device 203 used by the caregiver 104, such as a smartphone, tablet, wearable computing device (e.g., a watch, glasses, or other type of wearable computing device), or another type of mobile computing device 203. For instance, the mobile computing device 203 can execute an application that guides the caregiver 104 in delivery of treatment, such as chest compressions, to the victim 102. We sometimes refer to the defibrillator 200 as storing and transmitting the information; however, the mobile computing device 203 can similarly store and transmit the information.

The defibrillator 200 is connected to electrode pads 110 placed on the victim's chest via one or more cables 112. The defibrillator 200 provides defibrillation to the victim 102 as needed via the electrode pads 110 and instructs the caregiver 104 in performing CPR. The defibrillator 200 stores information indicative of the performance of the caregiver 104 and/or information indicative of the health status of the victim 102. For instance, the defibrillator 200 can store information indicative of the quality of chest compressions delivered to the victim 102 (e.g., as determined based on compression rate, compression depth, and/or other metrics), the duration of CPR, the duration of ventilations delivered to the victim 102, or other information indicative of the performance of the caregivers. The defibrillator 200 can store information indicative of the victim's vital signs, such as the victim's pulse, blood pressure, respiration rate, SpO2 level, CO2 data, information associated with the victim's cardiac rhythm (e.g., the victim's electrocardiogram (ECG) trace), or other information indicative of the health status of the victim 102. In some cases, the defibrillator 200 can receive some of the information indicative of the victim's vital signs from other victim monitoring devices.

The defibrillator 200 can transmit the stored information indicative of the performance of the caregiver 104 and/or the information indicative of the health status of the victim 102 to a display interface 210 of the defibrillator or to another computing device. For instance, representations of one or more portions of the victim's ECG trace can be transmitted to the display interface 210 of the defibrillator 200 or to another computing device. The information can be transmitted during treatment of the victim 102 or following treatment of the victim 102, e.g., when the defibrillator 200 is disconnected from the victim 102.

In some cases, the defibrillator 200 can transmit the information to a computing device at the rescue scene, such as a mobile computing device (e.g., a smartphone, a tablet, a wearable computing device such as a watch or glasses, or another type of mobile computing device), a laptop computer, another defibrillator, or another type of computing device. Transmitting information to a computing device at the rescue scene can be useful, e.g., to help a highly trained caregiver (e.g., a paramedic, an EMT, an advanced life support team, or another trained caregiver) to understand the history of the victim's treatment and health by a first responder prior to the trained caregiver's arrival.

The information can be transmitted to a remote computing device, such as a laptop or desktop computer, a server (e.g., a cloud-based server or a server dedicated to a facility such as a hospital, a defibrillator company, or an ambulance service), or another type of computing device. Transmitting information to a remote computing device that is not at the rescue scene can be useful, e.g., to allow medical professionals at a hospital to understand the history of the victim's treatment and health prior to the victim's arrival in the hospital without having to access the defibrillator 200 that was used to treat the victim.

Figure 2:
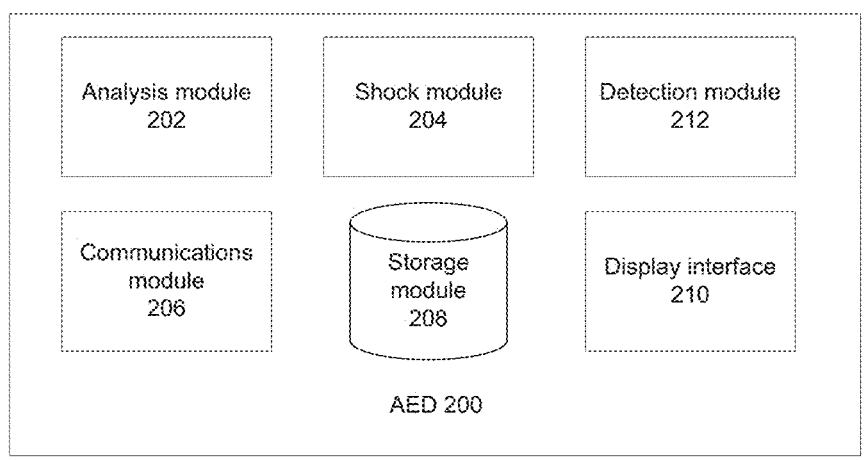
FIG. 2 is a block diagram of a defibrillator.

Referring to FIG. 2, the defibrillator 200 includes an analysis module 202 that determines whether the cardiac rhythm of the victim 102 is shockable. In one example, the analysis module 202 periodically (e.g., every minute, every 2 minutes, every 3 minutes, or another time period) monitors and analyzes the victim's rhythm for a short analysis period (e.g., 9 seconds, 12 seconds, 15 seconds, or another analysis period). The analysis module 202 identifies the victim's rhythm during the analysis period and determines whether the rhythm is shockable, for instance, based on characteristics of the waveform(s) in the rhythm. Example shockable rhythms (i.e., rhythms that can be treated by delivering a shock to the victim 102) include ventricular fibrillation, ventricular tachycardia, ventricular flutter, and other types of shockable rhythms. Example non-shockable rhythms (i.e., rhythms that cannot be treated effectively by delivering a shock to the victim 102) include asystole, bradycardia, pulseless electrical activity (PEA), idio-ventricular rhythms, normal rhythm, and other types of non-shockable rhythms.

If the victim's rhythm is shockable, a shock module 204 of the defibrillator 200 causes a shock to be delivered to the victim 102 through the electrode pads 110. In some cases, the shock can be delivered automatically. In some cases, a communications module 206 of the defibrillator 200 can prompt the caregiver 104 for a command to deliver a shock to the victim 102 or can present a "Clear" warning to the caregiver 104. If the victim's rhythm is non-shockable, the communications module 206 can instruct the caregiver to deliver chest compressions to the victim 102.

A treatment event is a determination (e.g., by the analysis module 202) of whether the victim's cardiac rhythm is shockable, e.g., following each analysis period or following an initial analysis period upon beginning treatment of the victim 102 with the defibrillator 200. The portion of the ECG trace associated with each treatment event can correspond to the analysis period preceding the treatment event. The portion of the ECG trace associated with a particular treatment event can be of a predetermined length of time (e.g., the length of the analysis period, such as 9 seconds, 12 seconds, 15 seconds, or another length of time) and can have a start time and an end time based on a time associated with the particular treatment event. For instance, the end time of the portion of the ECG trace associated with a particular treatment event can be the time at which the treatment event occurred (e.g., the time at which the victim's rhythm was determined to be shockable or non-shockable), and the start time of the portion of the ECG trace can be earlier by the length of the analysis period (e.g., 9 seconds, 12 seconds, 15 seconds, or another amount of time earlier).

The analysis module 202 can identify the portion of the victim's ECG trace associated with one or more treatment events that occurred during treatment of the victim 102 with the defibrillator 200. For instance, based on information indicative of the time at which a particular treatment event occurred and the length of time of the analysis period, the analysis module 202 can select the portion of the ECG trace that is associated with that particular treatment event.

A storage module 208 in the defibrillator 200 stores the information indicative of the performance of the caregiver 104 and/or the information indicative of the health status of the victim 102, such as the victim's ECG trace. The storage module 208 can be, e.g., a database, a file, or another type of data structure. In some examples, one or more portions of the ECG trace are stored, such as portions identified by the analysis module 202 as associated with treatment events. In some examples, the entire ECG trace is stored and each portion identified by the analysis module 202 as associated with a treatment event is marked, e.g., with a tag identifying the respective treatment event (e.g., a timestamp or a characteristic of the treatment event, such as an indication of whether the treatment event determined that the rhythm was shockable or non-shockable). In some examples, other data can also be stored. For instance, information from other victim monitoring devices, such as $SpO_2$ data, $CO_2$ data, ventilation data, chest compression data, and other data about the rescue attempt can be stored. In some examples, these data can be stored synchronously with the victim's ECG trace. In some examples, a narrative can be stored with the stored information, e.g., with the victim's ECG trace. For instance, the communications module 206 can record the caregiver's comments and the recorded comments can be stored synchronously with the victim's ECG trace or other information.

The stored information, such as the victim's ECG trace, can provide information that can be used to aid in diagnosing and treating the victim. For instance, the victim's ECG trace prior to receiving a shock can provide information that can be used to diagnose the victim's condition. Knowledge of the victim's likely diagnosis can inform treatment of the victim, both at the rescue scene 100 and in a hospital setting.

The portion of the ECG trace associated with an initial treatment event (e.g., corresponding to an initial treatment period during which the AED 200 was first connected to the victim 102, such as within the first 6-10 seconds) can provide information about the victim's pathology. For instance, this initial portion of the ECG trace can help to identify the victim's pathology as pulseless electrical activity (PEA), ST-elevation myocardial infarction (STEMI), ventricular arrhythmia, atrial arrhythmia, preeclampsia, or another cardiac pathology. If the victim's pathology can be identified, appropriate treatment can be delivered to the victim.

The portion of the ECG trace associated with each analysis period (e.g., the portion of the ECG trace during the analysis period prior to delivery of a shock or determination that the rhythm is non-shockable) can provide information about the types of rhythms that developed in the victim. In some cases, a shockable rhythm that occurs once in a victim may not occur again after defibrillation. Storing the ECG traces prior to delivery of a shock can serve as a catalog of the types of rhythms that developed in the victim, even if those rhythms occur only once or a small number of times. Knowledge of the rhythms that developed in the victim can inform decisions about diagnosis and treatment of the victim.

The communications module 206 causes some or all of the stored information, such as representations of the stored portions of the ECG trace, to be transmitted, e.g., to the display interface 210 of the defibrillator 200, such as a liquid crystal display (LCD) screen or another type of display interface; or to another computing device. For instance, information can be transmitted to a computing device used by a caregiver at the rescue scene 100 or a medical professional at a hospital. For instance, the transmitted portions of the ECG trace can be displayed on the display interface 210 of the defibrillator or on another computing device as still images or can be played back as videos.

In some examples, a representation of the portion of the ECG trace for one or more treatment events (e.g., the initial treatment period and/or one or more of the analysis periods) is automatically presented sequentially on the display interface 210. For instance, the representation of the portion of the ECG trace can be the portion of the ECG trace itself. In some examples, identifiers of multiple treatment events (e.g., identifiers indicative of the time of each treatment event) are displayed on the display interface 210, e.g., as a list, and the caregiver 102 can select to view the portions of the ECG trace for one or more of the listed treatment events. In some examples, identifiers of the types of rhythms exhibited by the victim 102 are displayed on the display interface 210, e.g., as a list, and the caregiver 102 can select to view all of the portions of the ECG trace associated with a particular type of rhythm, such as all shockable rhythms, all non-shockable rhythms, or a specific type of rhythm (e.g., ventricular fibrillation, asystole, or another specific type of rhythm).

The caregiver 104 can interact with the displayed portions of the ECG trace, e.g., to move forwards or backwards in time along a trace, to zoom in, to switch from the trace of one analysis period to the trace of another analysis period, etc. In some examples, the caregiver 104 can interact with the display interface 210 by clicking on the display interface 210 with a mouse or other pointing device, by typing commands into a keyboard or a keypad, or by using buttons provided on the defibrillator 200. In some examples, the display interface 210 is a touch-responsive interface, and the caregiver 104 can interact with the display interface 210 by touching, tapping, or dragging on the display interface 210 with a finger or stylus. In some examples, the defibrillator 200 includes voice recognition capabilities and the caregiver 104 can interact with the display interface 210 by speaking commands.

In some examples, the stored information can be displayed on the display interface 210 responsive to a user request. For instance, during or after treatment of the victim 102, a caregiver can request to view the stored portions of the ECG trace, e.g., to see the history of the victim's treatment.

Figure 1B:
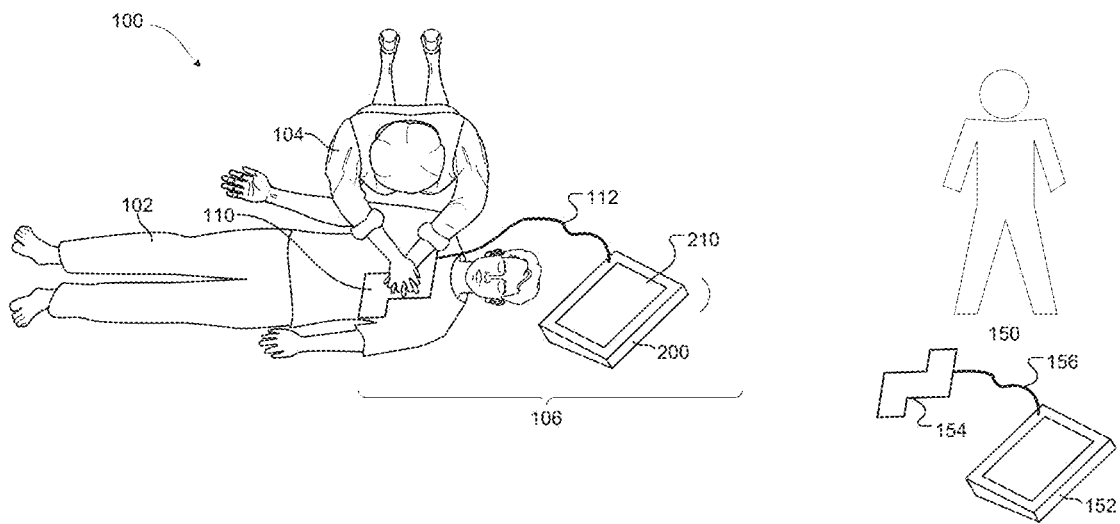

In some examples, the stored information, such as the stored portions of the ECG trace, can be displayed on the display interface 210 once the defibrillator 200 has been disconnected from the victim 102. For instance, referring to FIG. 1B, if a highly trained second caregiver 150 (e.g., a paramedic, an EMT, an advanced life support team, or another trained caregiver) arrives at the rescue scene 100, it can be beneficial for the second caregiver 150 to understand the history of the victim's 102 cardiac rhythms. This information can include the rhythms present at key times during the treatment, such as when treatment was first initiated and when the rhythms were identified as shockable or non-shockable. The rhythms during these periods can be displayed to the second caregiver 150.

Particularly, in some examples, the second caregiver 150 can arrive with a more advanced defibrillator 152. The caregiver 104 can stop treating the victim 102 with the defibrillator 200 and allow the second caregiver 150 to take over treatment using the advanced defibrillator 152. The second caregiver 150 can remove the electrode pads 110 from the victim 102, thus disconnecting the defibrillator 200 from the victim 102. The second caregiver can then position new electrode pads 154 on the victim 102 that are connected to the advanced defibrillator 152 via cables 156. In some cases, the electrode pads 110 are compatible with the advanced defibrillator 152, and the second caregiver 150 can disconnect the cables 112 from the defibrillator 200 (thus disconnecting the defibrillator 200 from the victim 102) and connect the cables 112 to the same advanced defibrillator 152.

Referring again to FIG. 2, a detection module 212 detects when the defibrillator 200 is disconnected from the victim 102. For instance, the detection module 212 can detect when a significant change occurs in the impedance across the victim's chest between the two electrode pads 110 by detecting a loss of impedance in a circuit that includes the defibrillator 200 and the victim 102. That is, when the electrode pads 110 are removed from the victim 102 or when the cables 112 are disconnected from the electrode pads 110, the detection module 212 detects a corresponding loss of impedance. Based on the loss of impedance, the detection module 212 determines that the defibrillator 200 has been disconnected from the victim 102. For instance, the detection module 212 can detect when the loss of impedance is greater than a threshold change or when the actual impedance falls below a threshold value. The threshold change or threshold value can be set such that small changes in impedance, e.g., due to cardiac activity of the victim, the victim's respiration or ventilation, or other activities, do not register as a disconnection of the defibrillator 200.

When the detection module 212 detects that the defibrillator 200 has been disconnected, the communications module 206 can ask for confirmation that treatment with the defibrillator has been completed. Once confirmation is received, the communications module 206 causes the information, such as the stored portions of the victim's ECG trace, to be transmitted. In one example, a confirmation message is displayed on the display interface 210 asking a caregiver (e.g., caregiver 104 or 150) to confirm that treatment with the defibrillator 200 has ended. In one example, an audio confirmation message can be played through a speaker in the defibrillator 200 and a caregiver can respond verbally. The caregiver's verbal response can be processed by voice recognition software implemented in the communications module 206.

In some examples, the communications module 206 can ask for confirmation as soon as the detection module 212 detects a loss of impedance. In some examples, the communications module 206 can ask for confirmation after a waiting period, such as 2 seconds, 5 seconds, or 10 seconds after the detection module 212 detects a loss of impedance. The waiting period can help avoid asking the caregiver for confirmation in response to an accidental disconnection of the defibrillator 200 (e.g., by accidentally dislodging a cable 112).

The ability to view information indicative of the performance of the caregiver 104 and/or the information indicative of the health status of the victim 102, such as portions of the victim's ECG trace, at the rescue scene can provide critical, lifesaving information to the caregivers at the rescue scene 100. For instance, the initial caregiver 104 may be a relatively untrained caregiver who does not know how to read ECG traces. That is, the caregiver 104 may be unable to communicate information about his own performance or about the health status of the victim, such as the victim's initial ECG trace and information about the portions of the ECG trace in the analysis periods, to the highly trained caregiver 150. By providing the caregiver 150 with the ability to view this information (e.g., portions of the victim's ECG trace), the caregiver 150 has rapid access to information that can enable him to make more informed decisions about treatment options for the victim 102 (e.g., information about the victim's condition when he first collapsed, information about the rhythms that triggered shock events, information about treatment that had previously been delivered to the victim, or other information). For instance, the caregiver 150 can use this information to decide which medications to administer, whether to continue with CPR or defibrillation treatment, how urgently to bring the victim to an emergency room, and other decisions. In addition, the caregiver 150 can communicate this information to other medical personnel, such as emergency room nurses or physicians, without having to download the ECG traces or transport the defibrillator 200 itself to the emergency room.

In some examples, the communications module 206 provides the ability to download portions of the victim's ECG trace and other monitoring data to a computing device, such as a mobile computing device (e.g., a laptop computer, a mobile phone, a tablet, a watch, glasses, or another type of mobile computing device) or to a storage device, such as a USB drive. For instance, the computing device or storage device can be connected to a data port on the defibrillator 200, e.g., directly or via a cable connection. In some examples, the portions of the victim's ECG trace can be downloaded through a wireless connection between the defibrillator 200 and the computing device, e.g., through a short-range wireless protocol such as Bluetooth® communication or another type of wireless communication. For instance, the victim's traces and other monitoring data can be downloaded to a computer at a hospital to allow a physician to view details of the victim's treatment history.

In some examples, the information indicative of the performance of the caregiver 104 and/or the information indicative of the health status of the victim 102 can be transmitted to a cloud-based server for storage. The information can be transmitted along with an identifier of the victim. The stored information can be encrypted, password-protected, or otherwise protected to maintain the security and privacy of the victim's information. A user, such as a medical professional in an emergency room, can view or download the victim's information with proper authorization, e.g., with knowledge of the victim's identifier, with possession of the appropriate encryption key or password, or with another type of authorization.

Figure 3:
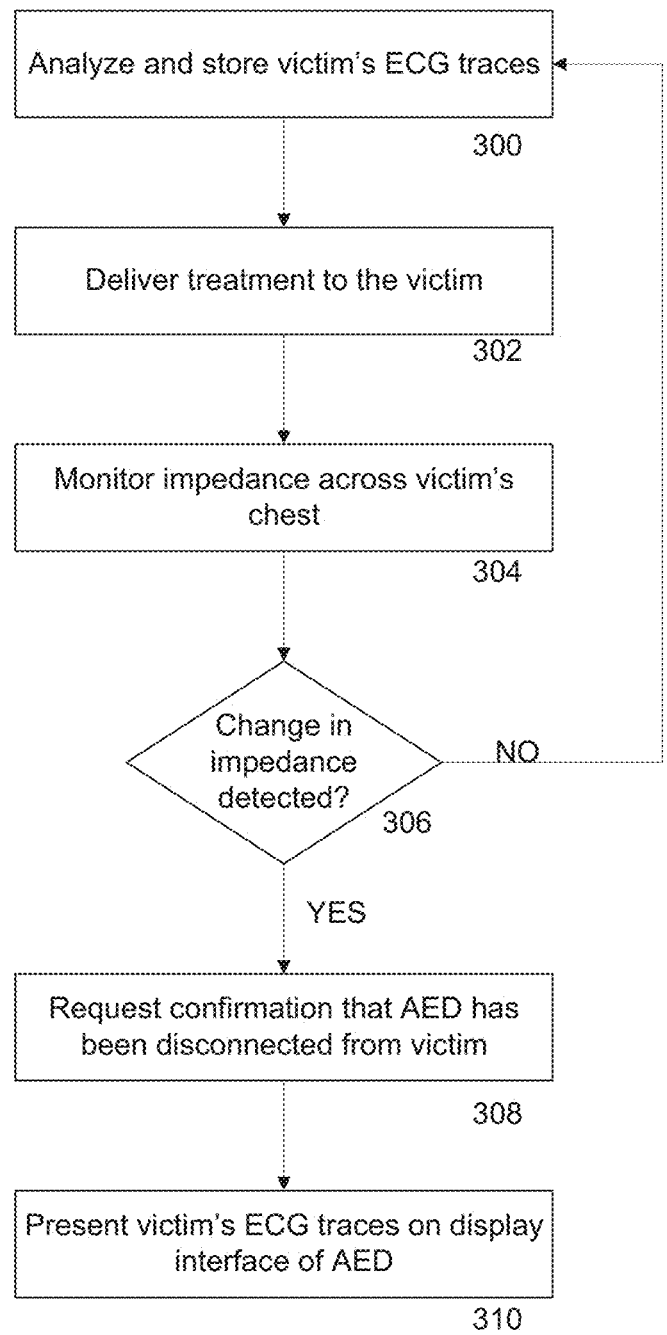
FIG. 3 is a flowchart.

Referring to FIG. 3, in one example of an approach to providing care to a victim, an AED or another type of defibrillator analyzes, identifies, and stores portions of a victim's ECG trace during treatment of the victim with the AED, e.g., while the AED is connected to the victim (300). Other monitoring data, and other monitoring information, such as $SpO_2$ data, $CO_2$ data, ventilation data, chest compression data, and other data about the rescue attempt, can also be stored synchronously with the portions of the victim's ECG trace. For instance, the AED analyzes the victim's rhythms periodically, e.g., once per minute, once every 2 minutes, once every 3 minutes, or another time period. The analysis period can be, e.g., 9 seconds, 12 seconds, 15 seconds, or another analysis period. The analysis of the victim's rhythms includes identify the type of rhythm and determining whether the rhythm is shockable or non-shockable. The portions of the ECG trace for at least each analysis period are stored on the AED Treatment is delivered to the victim (302). For instance, if the victim's rhythm is shockable, the AED can deliver a shock to the victim. The AED can instruct a caregiver to deliver chest compressions to the victim, e.g., following delivery of a shock or if the victim's rhythm is non-shockable.

During the treatment of the victim, the impedance across the victim's chest is monitored (304). For instance, the impedance across the victim's chest can be monitored continuously or periodically, e.g., once per second, once every 2 seconds, once every 5 seconds, or another time period. If no significant change in impedance is detected (306), the analysis and storage of the victim's rhythms (300) and the delivery of treatment (302) continue.

When a significant change in impedance is detected (306), the AED asks for confirmation that the AED has been disconnected from the victim (308). In some examples, the AED asks for confirmation after a waiting period of, e.g., 10 seconds after detecting a significant change in the impedance. The significant change in impedance can include that the change in impedance is greater than a threshold change in impedance or that the absolute value of the impedance is less than a threshold value. This significant change in impedance can indicate that the AED has been disconnected from the victim, e.g., by removing the electrode pads from the victim's chest or by disconnecting the electrode cables from the AED.

Upon receiving confirmation that the AED has been disconnected from the victim, the portions of the victim's ECG trace are presented on a display interface of the AED (310). In some examples, the portion of the ECG trace for each analysis period is automatically presented sequentially. In some examples, identifiers of treatment events associated with one or more of the analysis periods are displayed and a caregiver can select to view the portion of the ECG trace associated with one or more of the listed treatment events. In some examples, identifiers of one or more of the types of rhythms exhibited by the victim are displayed and a caregiver can select to view all of the portions of the ECG trace associated with a particular type of rhythm.

In some examples, some of the functionality of the AED 200 is carried out on a control device, such as a mobile device (e.g., a mobile phone, tablet, watch, glasses, or another type of mobile device). For instance, one or more of the analysis module 202, the communications module 206, the storage module 208, the display interface 210, and the detection module 212 can be implemented on the control device. An example control device is described in U.S. application Ser. No. 14/036,503, filed Sep. 25, 2013, the contents of which are incorporated herein by reference.

In some examples, a user of a mobile device can request to review the portions of the victim's ECG trace even if the AED has not been disconnected from the victim. For instance, while treatment is ongoing, a user can view the portions of the victim's ECG trace from earlier in treatment to gain an overview of how the victim's condition has progressed.

Figure 4:
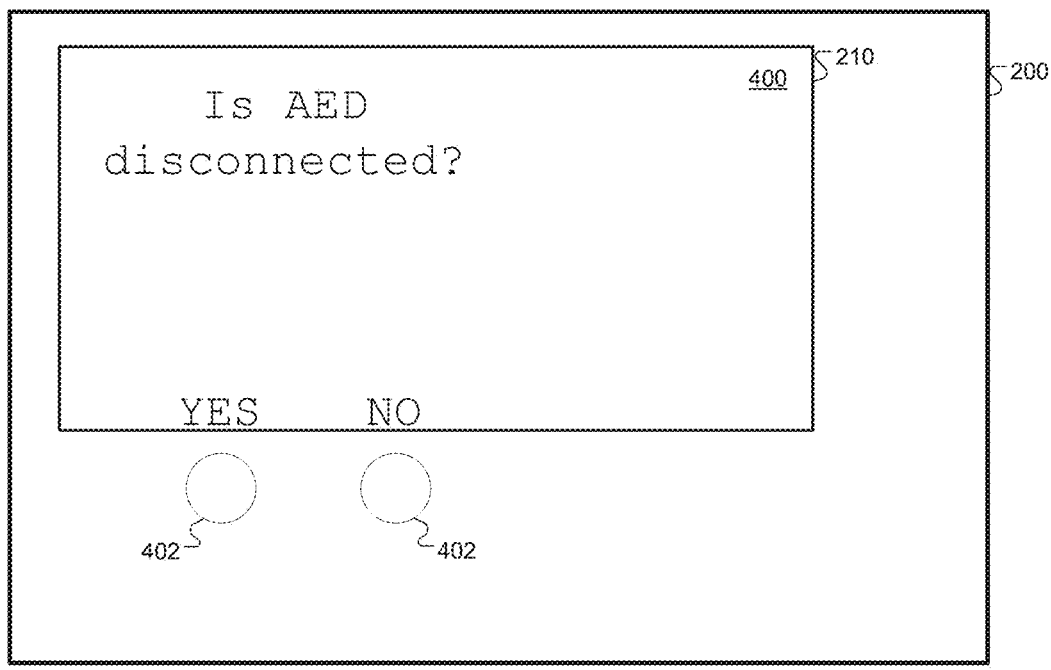
FIGS. 4-10 are screenshots.

Referring to FIG. 4, in one example, when a significant loss of impedance or other triggering event is detected, a confirmation screen 400 is displayed on the display interface 210 of the AED 200. The confirmation screen 400 asks a caregiver to confirm that the AED 200 has been disconnected from the victim. The caregiver can respond by touching or tapping on the display interface 210 or by pushing a button 402.

Figure 5:
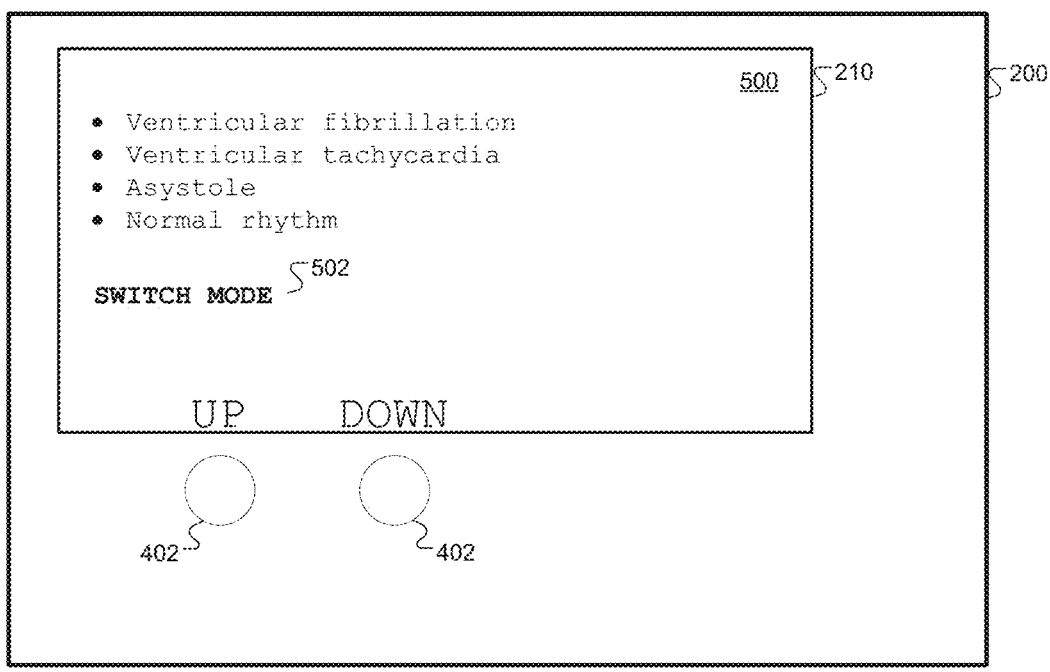

Referring to FIG. 5, in this example, after confirmation is received, a rhythms screen 500 displays a list of identifiers of all of the types of rhythms that occurred during treatment of the victim. The caregiver can select a type of rhythm to view the portions of the ECG traces in which the selected type of rhythm occurred by touching or tapping on the display interface or by pushing a button, if available. The caregiver can scroll up or down through the list of rhythms using the buttons 402. To view a chronological list of events (e.g., the timeline screen 800, described below) or a graphical timeline (e.g., the graphs screen 900, described below), the caregiver can select a "Switch Mode" option 502. In some examples, the types of rhythms that occurred during treatment of the victim are categorized as either "shockable" or "not shockable" on the rhythms screen 500.

Figure 6:
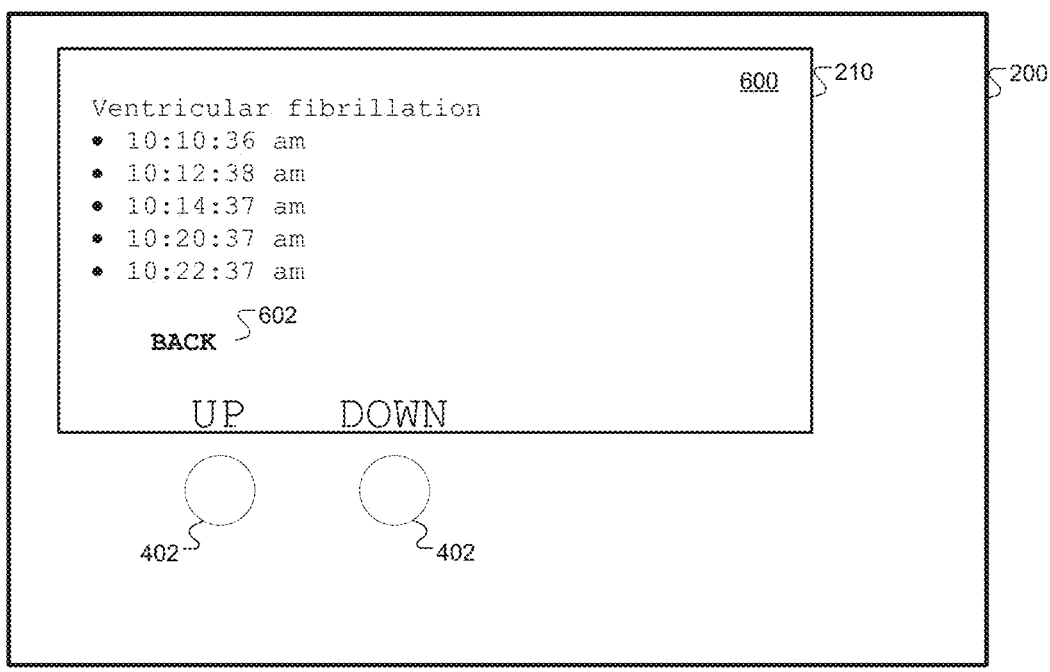

Referring to FIG. 6, in this example, the caregiver selected to view the portions of the ECG trace in which ventricular fibrillation was identified. An events screen 600 displays a list of all of the occurrences of ventricular fibrillation (e.g., all of the analysis periods in which ventricular fibrillation occurred). The occurrences can be identified by the number of the corresponding treatment event, by the timestamp of the corresponding treatment event, or by another identifier. In the example of FIG. 6, two periods of ventricular fibrillation occurred: one spanning three analysis periods between 10:10 and 10:14, and the second spanning two analysis periods between 10:20 and 10:22. The caregiver can select one of the treatment events to view the portion of the ECG trace associated with that treatment event (e.g., the portion of the ECG trace for the analysis period preceding the selected treatment event) by touching or tapping on the display interface. The caregiver can scroll up or down through the list of occurrences using the buttons 402. The caregiver can return to the rhythms screen 500 by selecting a "Back" option 602.

Figure 7:
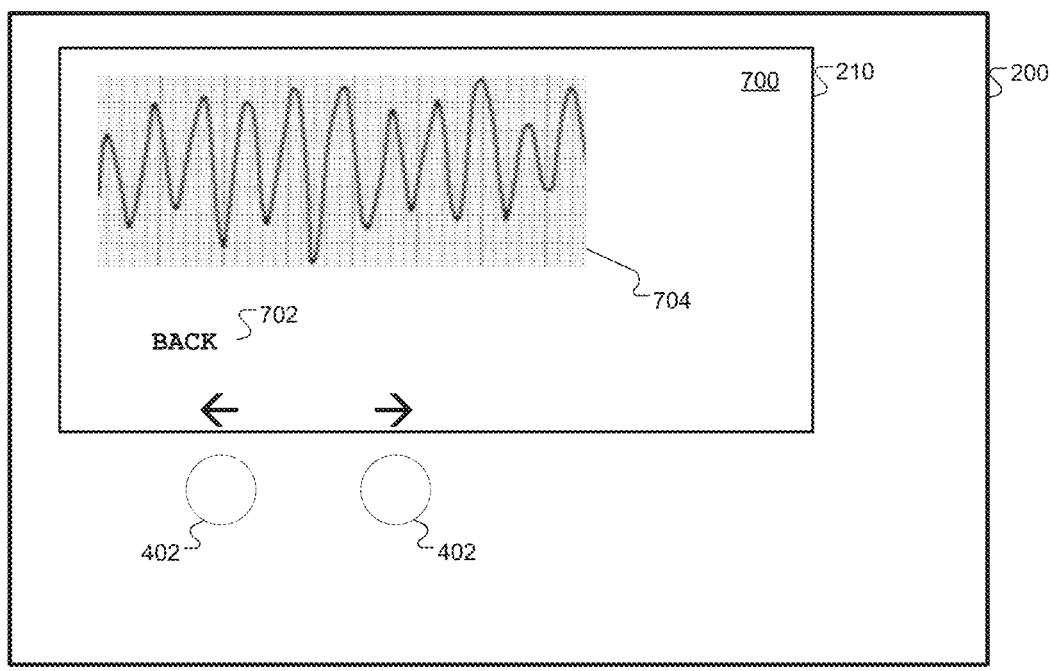

Referring to FIG. 7, in this example, the caregiver selected to view the first occurrence of ventricular fibrillation. A trace screen 700 displays a portion 704 of an ECG trace corresponding to this occurrence. In some examples, the caregiver can interact with the portion 704 of the ECG trace, e.g., by zooming in or out or scrolling forwards or backwards in time. From the trace screen 700, the caregiver can scroll to the trace for the previous analysis period or the next analysis period, e.g., by swiping to the right or left on the screen or by using the buttons 402. The caregiver can return to the previous screen by selecting a "Back" option 702.

Figure 8:
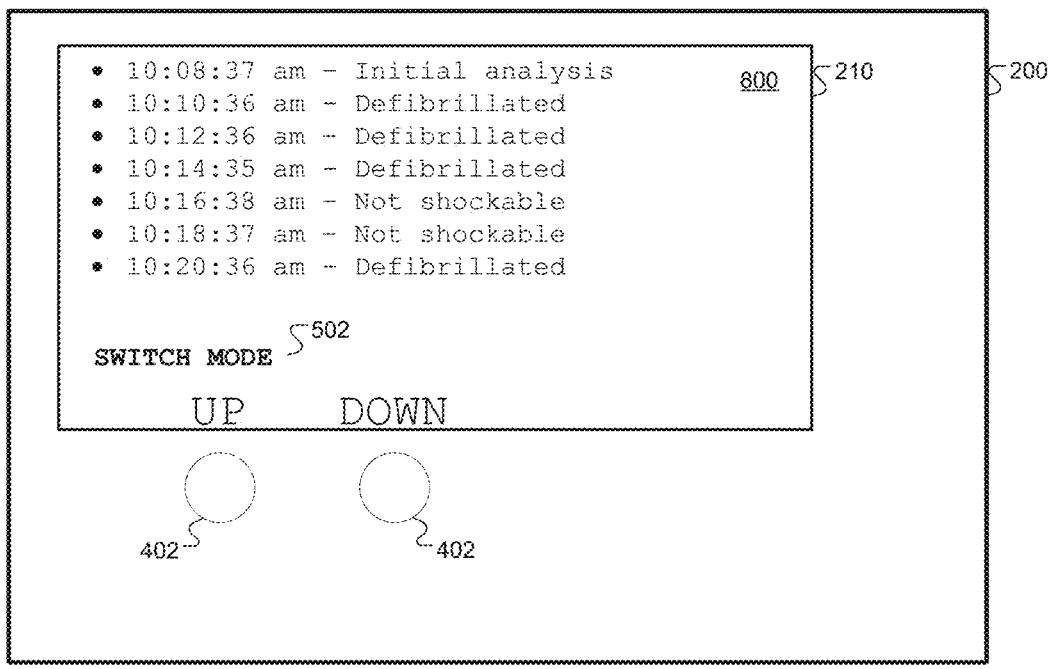

Referring to FIG. 8, in another viewing mode, a chronological list of treatment events can be displayed on a timeline screen 800. The timeline screen 800 displays a menu of identifiers of the treatment events in chronological order. The treatment events can be identified by number, by timestamp, or by another identifier. In some examples, the action taken at each treatment event (e.g., shock or no shock), the type of rhythm identified in the analysis period preceding each treatment event, or both can also be displayed. Selecting one of the treatment events brings up a display of the portion of the ECG trace associated with the selected treatment event, such as the portion of the ECG trace for the analysis period preceding the selected treatment event (e.g., such as trace screen 700). The caregiver can scroll up or down through the list of treatment events using the buttons 402. To view a list of the types of rhythms (e.g., the rhythms screen 500) or a graphical timeline (e.g., the graphs screen 900), the caregiver can select the "Switch Mode" option 502.

Figure 9:
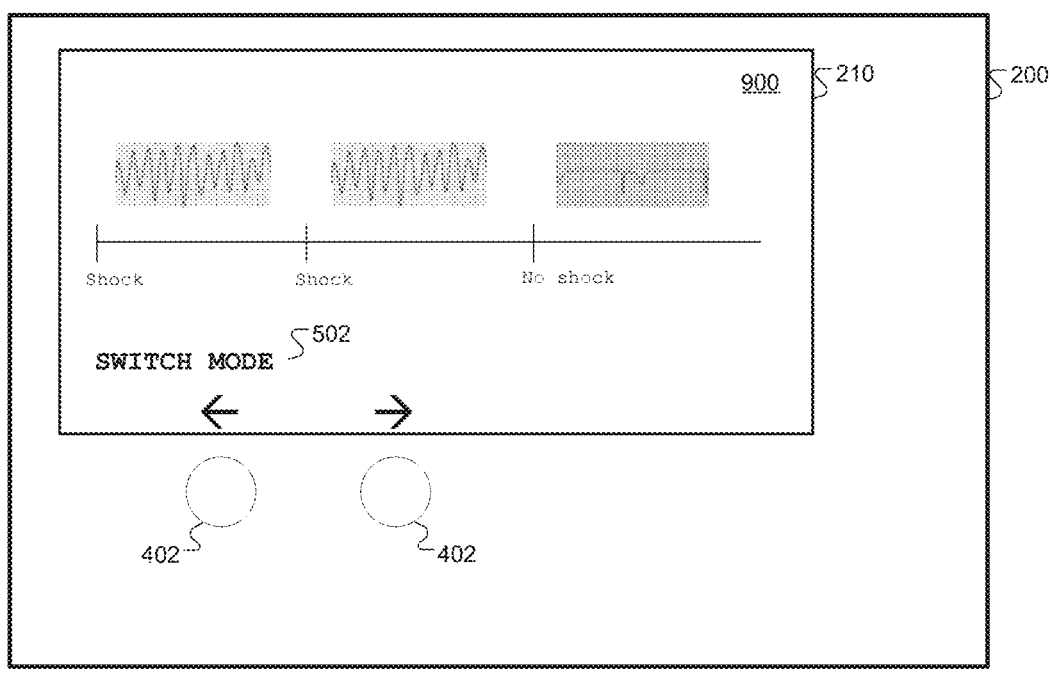

Referring to FIG. 9, in another viewing mode, a graphical timeline view of treatment events can be displayed on a graph screen 900. The graph screen displays a horizontal timeline of the treatment events in chronological order with a brief description of each treatment event. Selecting one of the treatment events brings up a display of the portion of the ECG trace associated with the selected treatment event, such as the portion of the ECG trace for the analysis period preceding the selected treatment event (e.g., such as trace screen 700). The caregiver can scroll forwards or backwards through the horizontal timeline using the buttons 402. To view a list of the types of rhythms (e.g., the rhythms screen 500), a textual timeline (e.g., the timeline screen 800), the caregiver can select the "Switch Mode" option 502.

Figure 10:
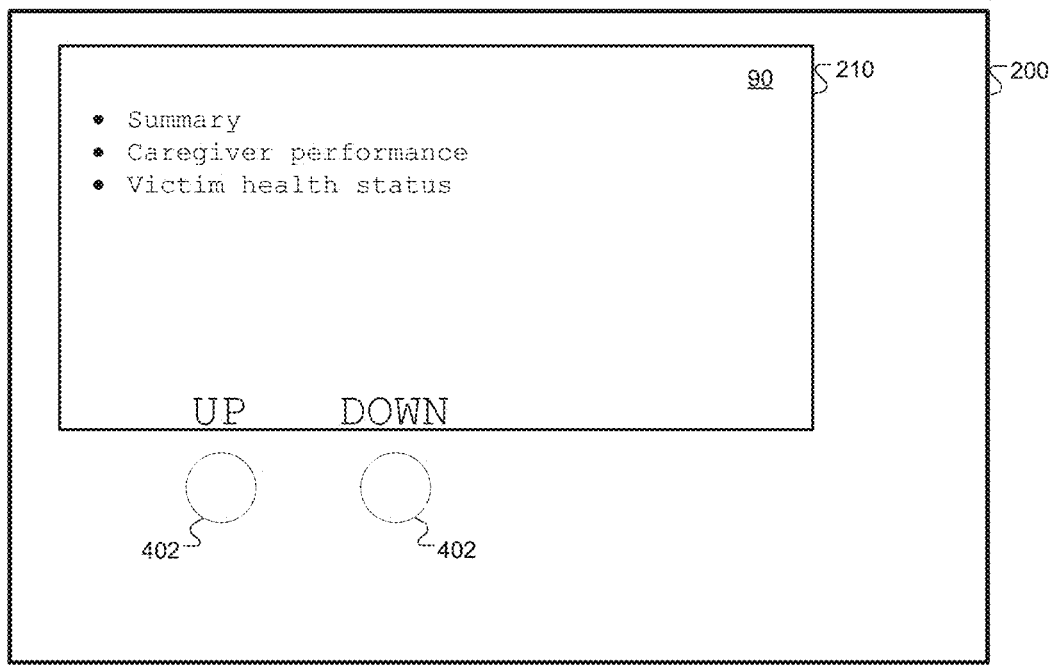

Referring to FIG. 10, in a general presentation screen 90, a menu is presented that displays options for viewing an overall summary of the victim's treatment, information indicative of the performance of a rescuer, or information indicative of the victim's health status. The overall summary can include a high-level presentation of summary information describing the treatment of the victim, such as a duration or general quality of CPR, a number of times the victim was shocked with a defibrillator, or another high-level summary. The information indicative of the performance of a rescuer can include more detailed information descriptive of the rescuer's treatment of the victim. The information indicative of the victim's health status can include more detailed data about the victim, such as the victim's vital signs, ECG trace, or other information.

The example screens shown in FIGS. 4-10 are screens on a defibrillator display interface. Similar information can also be displayed on other display interfaces, such as on the display screen of a mobile computing device, a laptop or desktop computer, a television, or another type of display screen.

Figure 11:
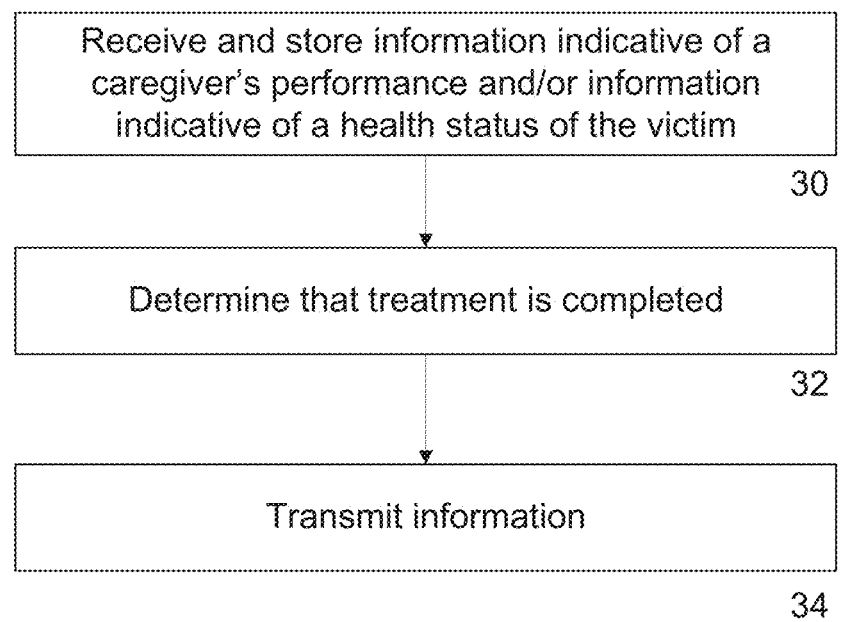
FIG. 11 is a flowchart.

Referring to FIG. 11, in an example of a general approach to providing care to a victim, a computing device receives and stores information indicative of a caregiver's performance and/or information indicative of a health status of the victim (30). In some instances, the computing device can be a defibrillator that stores portions of a victim's ECG trace as described above. The defibrillator can also store other information, such as vital signs of the victim, details about the quality and duration of compressions delivered to the victim, or other information. In some instances, the computing device can be a mobile computing device (e.g., a smartphone, tablet, wearable computing device such as a watch or glasses, or other type of mobile computing device) that executes an application to guide the caregiver in administering chest compressions to the victim. When placed on the victim (e.g., on the victim's chest) or held in the caregiver's hands, the application executing on the mobile computing device can detect information indicative of the caregiver's performance, such as the rate and depth of the compressions delivered to the victim, the length of time for which the caregiver performed chest compressions, or the nature of the CPR (e.g., continuous or occasional compressions).

The computing device determines that treatment of the victim by the caregiver using (or assisted by) the computing device is completed (32). Treatment of the victim by the caregiver may be completed, e.g., if a more highly trained caregiver arrives to take over for a less trained first responder, if the victim arrives by ambulance at an emergency room, or for another reason. If the computing device is a defibrillator, the defibrillator can detect a significant change in impedance indicative of removal of electrodes from the victim's chest. If the computing device is a mobile computing device, the mobile computing device can determine that treatment is completed when the caregiver enters an input (e.g., when the caregiver pushes a "stop" icon or closes the application). In some examples, the more highly trained caregiver may arrive with a computing device, such as an AED, that broadcasts a signal to cause a mobile computing device running the application to determine that its treatment is completed.

The stored information indicative of a caregiver's performance and/or information indicative of a health status of the victim are transmitted (34). In some examples, the information is transmitted to a display screen of the same computing device, such as to a display screen of the defibrillator or a display screen of the mobile computing device. In some examples, the information is transmitted to a local computing device. For instance, the mobile computing device can transmit its stored information to the AED brought by the more highly trained caregiver. In some examples, the information is transmitted to a remote computing device, such as to a server for storage.

Figure 12:
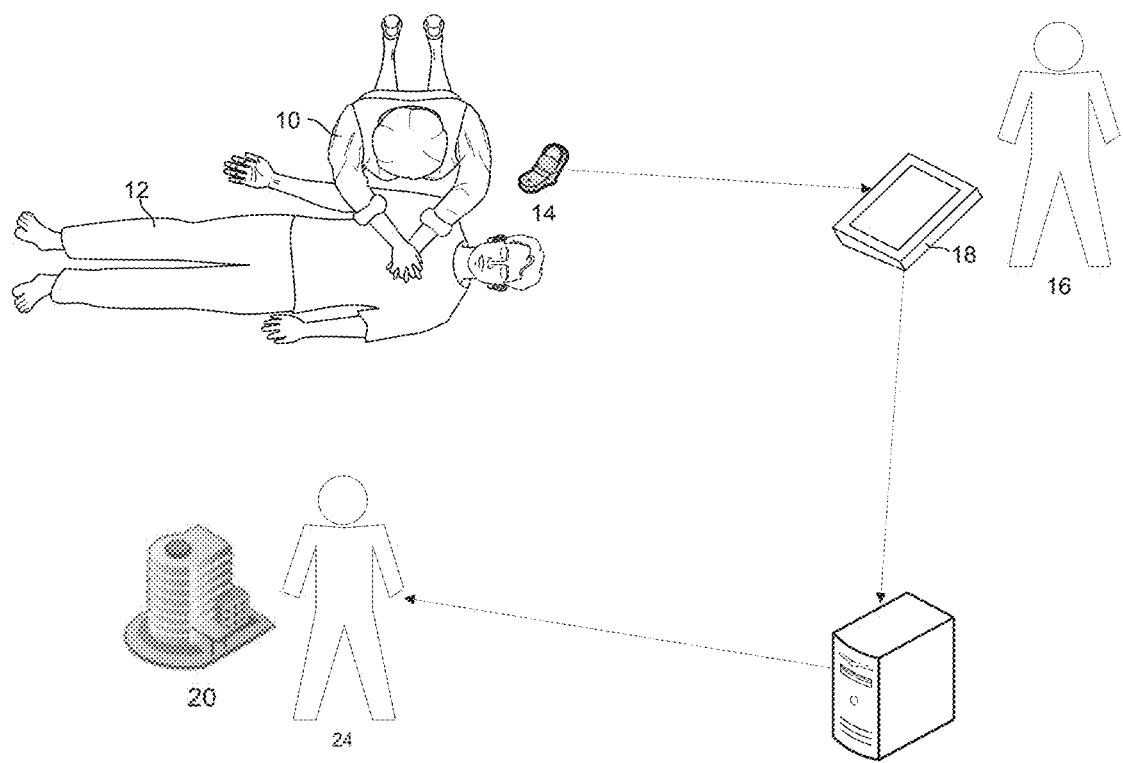
FIG. 12 is a diagram of a rescue scene.

Referring to FIG. 12, in a specific example, a bystander 10 encounters a victim 12 who appears to be in cardiac arrest. The bystander 10 calls 9-1-1 and, guided by an application executing on his mobile computing device 14, administers chest compressions to the victim 12. When placed on the chest of the victim 12, the application executing on the mobile computing device 14 can detect information indicative of the bystander's performance, such as the rate and depth of the compressions delivered to the victim, the length of time for which the bystander 10 performed chest compressions, or the nature of the CPR (e.g., continuous or occasional compressions).

In this example, an EMT 16 arrives with an AED 18 and takes over care of the victim 12 from the bystander 10. The EMT 16 wants to know what sort of treatment the victim 12 received from the bystander 10, but the bystander 10 may lack the knowledge to describe his treatment, may be too overwhelmed to discuss the treatment, or may wish to leave the scene. The bystander's mobile computing device 14 can transmit the information indicative of the bystander's performance to the AED 18. A summary of the bystander's performance, based on the transmitted information, can be displayed on a display screen of the AED 18 to indicate to the EMT 16 that the bystander performed good quality, continuous chest compressions for the last two minutes at a generally constant rate and depth. Based on this summary, the EMT 16 can determine how to best continue treatment of the victim 12.

In this example, once the victim 12 is stabilized, the victim 12 is put into an ambulance and taken to an emergency room 20. In the ambulance, the victim 12 goes into cardiac arrest again and the EMT 16 defibrillates the victim using the AED 18, performs CPR, and restabilizes the victim 12. Once treatment of the victim with the AED 18 is completed, the AED can transmit information indicative of the EMT's performance and information indicative of the health status of the victim to a server 22 for storage. When the victim arrives in the emergency room 20, medical professionals 24 can view or download the information stored on the server 22 to understand the victim's treatment history. The information stored on the server 22 is accessible to the medical professionals 24 in the emergency room even after the EMT 16 has departed with the AED 18, thus allowing the emergency room professionals 24 to access the victim's information at a convenient and appropriate time.

In some examples, the transmission of the information indicative of treatment of a victim by a first caregiver or information indicative of a health status of a victim from a first computing device to a second computing device can occur without any intervention by a user of either device. For instance, each device may have been preconfigured to recognize the identity of the other device and establish communications with the other device. In some examples, the two devices can establish communications according to a communications protocol that is encrypted, e.g., to sufficiently protect the data and identity of the patient, such as a communications protocol that is encrypted in compliance with health data protection standards such as HIPAA (Health Insurance Portability and Accountability Act) regulations.

In some examples, the second device can be configured to maintain power and operations to an internal low power communication system that can remain operational even when the second device is functionally in an OFF state, e.g., when the second device is not providing any clinical functions to the user. The low power communications may use the Bluetooth low energy technology of Bluetooth 4.0, as described in the following (from http://www.bluetooth.com/Pages/Basics.aspx):

"The most commonly used radio is Class 2 and uses 2.5 mW of power. Bluetooth technology is designed to have very low power consumption. This is reinforced in the specification by allowing radios to be powered down when inactive. The Generic Alternate MAC/PHY in Version 3.0 HS enables the discovery of remote AMPs for high speed devices and turns on the radio only when needed for data transfer giving a power optimization benefit as well as aiding in the security of the radios. Bluetooth low energy technology, optimized for devices requiring maximum battery life instead of a high data transfer rate, consumes between ½ and 1/100 the power of classic Bluetooth technology."

In cases in which the internal low power communication system of the second device remains operational even when the second device is otherwise in the OFF state, data (e.g., the information indicative of treatment of a victim by a first caregiver or information indicative of a health status of a victim) can begin to be transmitted (e.g., downloaded) even if the second device is in the OFF state. For instance, if the second device is in the OFF state when a victim is transferred (e.g., transferred to another caregiver, such as from a first responder to a professional caregiver, or transferred by ambulance to an emergency room, or otherwise transferred), information indicative of the treatment of the victim and/or information indicative of the health status of the victim can still be transferred.

In some examples, the first device can upload data (e.g., the information indicative of treatment of a victim by a first caregiver or information indicative of a health status of a victim) to a remote storage facility, such as a cloud storage facility. In some cases, the data can be uploaded with an encryption mechanism, such as with an encrypted key that is specific to the combination of the particular first device and the particular victim. At the time of patient transfer, the first device can establish a connection with the second device and rapidly transfer the encrypted key to the second device, without needing to transfer all the data to the second device, which can be time consuming. The second device can then submit the encrypted key to the cloud storage facility to retrieve the relevant information for the specific first device-victim combination, which can then be displayed to the new caregiver. Once the encrypted key is transferred from the first device to the second device, the first device can be powered off or removed from the location (e.g., the rescue scene). The rapid transfer of only an encrypted key can thus enable the first device to be rapidly put back into service, e.g., on an ambulance.

The features described herein can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented on a mobile computing device, such as a mobile phone, a tablet, a watch, glasses, or another type of mobile computing device. The mobile computing device can have a display device such as a touch screen for displaying information to the user and receiving input from the user. The mobile computing device can receive input from the user via the touch screen, a key pad, a microphone, or another type of input device.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

It is to be understood that the foregoing description is intended to illustrate and not to limit the scope of the invention, which is defined by the scope of the appended claims. Other embodiments are within the scope of the following claims.

What is claimed is:

1. A system for reviewing patient information as a result of medical treatment, comprising:
   a defibrillation device comprising one or more electrodes;
   storage for storing one or more treatment profiles comprising patient treatment data;
   a display interface configured to present the patient treatment data of the one or more treatment profiles, wherein the patient treatment data comprises one or more representations of electrocardiogram (ECG) signals associated with the one or more treatment profiles;
   one or more controls configured to control presentation of the patient treatment data by the display interface; and
   at least one processor coupled to a memory, the at least one processor and the memory configured to perform operations comprising:
      receiving, from the defibrillation device, the patient treatment data comprising a plurality of ECG signals,
      storing, in a particular treatment profile of the storage, the plurality of ECG signals,
      retrieving, from the storage, particular patient treatment data of the particular treatment profile of the one or more treatment profiles, the particular patient treatment data comprising at least one ECG signal of the plurality of ECG signals,
      in response to receiving a first signal from the one or more controls, causing the display interface to present at least a first portion of the at least one ECG signal, the first portion corresponding to a first period of time, and
      in response to receiving a second signal from the one or more controls, causing the display interface to present at least a second portion of the at least one ECG signal, the second portion corresponding to a second period of time that is different from the first period of time,
      wherein the one or more controls are configured to enable selection of the at least one ECG signal from the plurality of ECG signals.

2. The system of claim 1, wherein display interface is configured to present the plurality of ECG signals as a list, and wherein the plurality of ECG signals are ordered chronologically in the list according to a time that each ECG signal of the plurality was generated.

3. The system of claim 1, wherein the at least one ECG signal is associated with an indicator indicative of whether the at least one ECG signal represents a shockable rhythm or a non-shockable rhythm, and wherein the display interface is configured to present the indicator in association with the at least one ECG signal.

4. The system of claim 1, wherein the at least one ECG signal is associated with a timestamp representing a time at which patient treatment data comprising at least one ECG signal is generated, and wherein the display interface is configured to present the timestamp in association with the at least one ECG signal.

5. The system of claim 1, wherein the particular patient treatment data comprises one or more of $SpO_2$ data, $CO_2$ data, ventilation data, chest compression data, and narrative data, wherein the particular patient treatment data is contemporaneous with a time period during which a portion of the at least one ECG signal is measured, and wherein the display interface is configured to present the particular patient treatment data in association with the portion of the at least one ECG signal in response to receiving a third signal from the one or more controls.

6. The system of claim 1, wherein the at least one ECG signal is associated with pathology data indicative of a cardiac pathology represented by the at least one ECG signal, the cardiac pathology comprising one or more of pulseless electrical activity (PEA), ST-elevation myocardial infarction (STEMI), ventricular arrhythmia, atrial arrhythmia, and preeclampsia, and wherein the display interface is configured to present the pathology data in association with the at least one ECG signal.

7. The system of claim 1, wherein the at least one ECG signal is associated with type data indicative of a type of rhythm represented by the at least one ECG signal, the type of rhythm comprising one or more of ventricular fibrillation and asystole rhythm, and wherein the display interface is configured to display the type data in association with the at least one ECG signal.

8. The system of claim 1, wherein a length of the at least one ECG signal corresponds to a predetermined length of time preceding a determination by a defibrillating device of whether to deliver shock therapy to a patient.

9. The system of claim 8, wherein the predetermined length of time is between approximately 9-15 seconds.

10. The system of claim 1, wherein the at least one the ECG signal corresponds to an initial treatment period during which a defibrillating device system is being connected to a patient.

11. The system of claim 1, wherein the operations comprise:
   filtering, in response to a third signal from the one or more controls, a plurality of ECG signals in the particular patient treatment data based on one or more of data indicative of a cardiac pathologies represented by each ECG signal of the plurality, data indicative of a type of rhythm represented by each ECG signal, a timestamp associated with each ECG signal, and narrative data associated with by each ECG signal; and
   causing the display interface to present one or more ECG signals of the particular patient treatment data that are filtered from the plurality of ECG signals.

12. The system of claim 1, wherein the operations comprise receiving data indicating that a defibrillating device is disconnected from a patient, and
   in response to receiving the data indicating that a defibrillating device is disconnected, transmitting the at least one ECG signal to at least one of the storage and the display interface for presentation of a representation of the at least one ECG signal.

13. The system of claim 1, wherein the operations comprise receiving data indicating that a treatment of a patient is completed, and
in response to receiving the data indicating that a defibrillating device is disconnected, transmitting the at least one ECG signal to at least one of the storage and the display interface for presentation of the particular patient treatment data comprising the at least one ECG signal.

14. The system of claim 1, wherein receiving, from the defibrillation device, the patient treatment data comprising the plurality of ECG signals comprises receiving the patient treatment data from a cloud computing system.

15. The system of claim 1, wherein receiving, from the defibrillation device, the patient treatment data comprising the plurality of ECG signals comprises receiving the patient treatment data from a physical connection to the defibrillation device.

16. One or more non-transitory computer readable media comprising instructions executable by one or more processors, the instructions configured to cause the one or more processors to perform operations comprising:
receiving, from a defibrillation device comprising one or more electrodes, patient treatment data comprising a plurality of ECG signals; and
storing, in a particular treatment profile, the plurality of ECG signals;
retrieving particular patient treatment data of the particular treatment profile, the particular patient treatment data comprising at least one ECG signal of the plurality of ECG signals;
in response to receiving a first signal from one or more controls, causing a display interface to present at least a first portion of the at least one ECG signal, the first portion corresponding to a first period of time; and
in response to receiving a second signal from the one or more controls, causing the display interface to present at least a second portion of the at least one ECG signal, the second portion corresponding to a second period of time that is different from the first period of time,
wherein the one or more controls are configured to enable selection of the at least one ECG signal from the plurality of ECG signals.

17. The one or more non-transitory computer readable media of claim 16, wherein display interface is configured to present the plurality of ECG signals as a list, and wherein the plurality of ECG signals are ordered chronologically in the list according to a time that each ECG signal of the plurality was generated.

18. The one or more non-transitory computer readable media of claim 16, wherein the at least one ECG signal is associated with an indicator indicative of whether the at least one ECG signal represents a shockable rhythm or a non-shockable rhythm, and wherein the display interface is configured to present the indicator in association with the at least one ECG signal.

19. The one or more non-transitory computer readable media of claim 16, wherein the at least one ECG signal is associated with a timestamp representing a time at which patient treatment data comprising at least one ECG signal is generated, and wherein the display interface is configured to present the timestamp in association with the at least one ECG signal.

20. The one or more non-transitory computer readable media of claim 16, wherein the particular patient treatment data comprises one or more of $SpO_2$ data, $CO_2$ data, ventilation data, chest compression data, and narrative data, wherein the particular patient treatment data is contemporaneous with a time period during which a portion of the at least one ECG signal is measured, and wherein the display interface is configured to present the particular patient treatment data in association with the portion of the at least one ECG signal in response to receiving a third signal from the one or more controls.

21. The one or more non-transitory computer readable media of claim 16, wherein the at least one ECG signal is associated with pathology data indicative of a cardiac pathology represented by the at least one ECG signal, the cardiac pathology comprising one or more of pulseless electrical activity (PEA), ST-elevation myocardial infarction (STEMI), ventricular arrhythmia, atrial arrhythmia, and preeclampsia, and wherein the display interface is configured to present the pathology data in association with the at least one ECG signal.

22. The one or more non-transitory computer readable media of claim 16, wherein the at least one ECG signal is associated with type data indicative of a type of rhythm represented by the at least one ECG signal, the type of rhythm comprising one or more of ventricular fibrillation and asystole rhythm, and wherein the display interface is configured to display the type data in association with the at least one ECG signal.

23. The one or more non-transitory computer readable media of claim 16, wherein a length of the at least one ECG signal corresponds to a predetermined length of time preceding a determination by a defibrillating device of whether to deliver shock therapy to a patient.

24. The one or more non-transitory computer readable media of claim 23, wherein the predetermined length of time is between approximately 9-15 seconds.

25. The one or more non-transitory computer readable media of claim 16, wherein the at least one the ECG signal corresponds to an initial treatment period during which a defibrillating device system is being connected to a patient.

26. The one or more non-transitory computer readable media of claim 16, wherein the operations comprise:
filtering, in response to a third signal from the one or more controls, a plurality of ECG signals in the particular patient treatment data based on one or more of data indicative of a cardiac pathologies represented by each ECG signal of the plurality, data indicative of a type of rhythm represented by each ECG signal, a timestamp associated with each ECG signal, and narrative data associated with by each ECG signal; and
causing the display interface to present one or more ECG signals of the particular patient treatment data that are filtered from the plurality of ECG signals.

27. The one or more non-transitory computer readable media of claim 16, wherein the operations comprise receiving data indicating that a defibrillating device is disconnected from a patient, and
in response to receiving the data indicating that a defibrillating device is disconnected, transmitting the at least one ECG signal to at least one of a storage and the display interface for presentation of a representation of the at least one ECG signal.

28. The one or more non-transitory computer readable media of claim 16, wherein the operations comprise receiving data indicating that a treatment of a patient is completed, and
in response to receiving the data indicating that a defibrillating device is disconnected, transmitting the at least one ECG signal to at least one of a storage and the display interface for presentation of the particular patient treatment data comprising the at least one ECG signal.

29. The one or more non-transitory computer readable media of claim 16, wherein receiving, from the defibrillation device, the patient treatment data comprising the plurality of ECG signals comprises receiving the patient treatment data from a cloud computing system.

30. The one or more non-transitory computer readable media of claim 16, wherein receiving, from the defibrillation device, the patient treatment data comprising the plurality of ECG signals comprises receiving the patient treatment data from a physical connection to the defibrillation device.

* * * * *